US007484509B2

(12) United States Patent
Schubert

(10) Patent No.: US 7,484,509 B2
(45) Date of Patent: Feb. 3, 2009

(54) FILTER AND BLOWER UNIT FOR BREATHING MASKS OR BONNETS

(75) Inventor: Axel Schubert, Berlin (DE)

(73) Assignee: MSA Auer GmbH (DE)

( * ) Notice: Subject to any disclaimer, the term of this patent is extended or adjusted under 35 U.S.C. 154(b) by 479 days.

(21) Appl. No.: 10/542,689

(22) PCT Filed: Dec. 19, 2003

(86) PCT No.: PCT/DE03/04267

§ 371 (c)(1),
(2), (4) Date: Jul. 19, 2005

(87) PCT Pub. No.: WO2004/071583

PCT Pub. Date: Aug. 26, 2004

(65) Prior Publication Data

US 2007/0119452 A1 May 31, 2007

(30) Foreign Application Priority Data

Feb. 17, 2003 (DE) ................................ 103 07 330

(51) Int. Cl.
*A61M 11/00* (2006.01)

(52) U.S. Cl. ............................. 128/205.29; 128/205.27

(58) Field of Classification Search ............ 128/205.27, 128/205.29–206.19
See application file for complete search history.

(56) References Cited

U.S. PATENT DOCUMENTS

| | | | | |
|---|---|---|---|---|
| 4,320,755 A | | 3/1982 | Flint et al. | |
| 4,633,868 A | * | 1/1987 | Itoh et al. | 128/204.26 |
| 5,072,728 A | * | 12/1991 | Pasternack | 128/204.18 |
| 5,973,424 A | | 10/1999 | Engelberger et al. | |
| 6,032,668 A | * | 3/2000 | Chung | 128/206.27 |

FOREIGN PATENT DOCUMENTS

| | | |
|---|---|---|
| DE | 197 46 605 | 6/1998 |
| GB | 2 338 655 | 12/1999 |

* cited by examiner

*Primary Examiner*—Steven O Douglas
(74) *Attorney, Agent, or Firm*—Wood, Phillips, Katz, Clark & Mortimer

(57) ABSTRACT

A direct current motor having a fixed stator coil module and a magnetic rotor that can be rotated around the perimeter of said module and forming an impeller at the same time. The coils, terminal and electric connecting lines as well as upstream motor control and voltage converter modules are embedded in a non-conductive casting compound. Power is supplied from an intrinsically safe accumulator or battery pack at a voltage that is still considered intrinsically safer using a higher current value to match the required motor output. The filter and blower unit can be used in zone "0" potentially explosive atmospheres.

5 Claims, 1 Drawing Sheet

FIG. 2
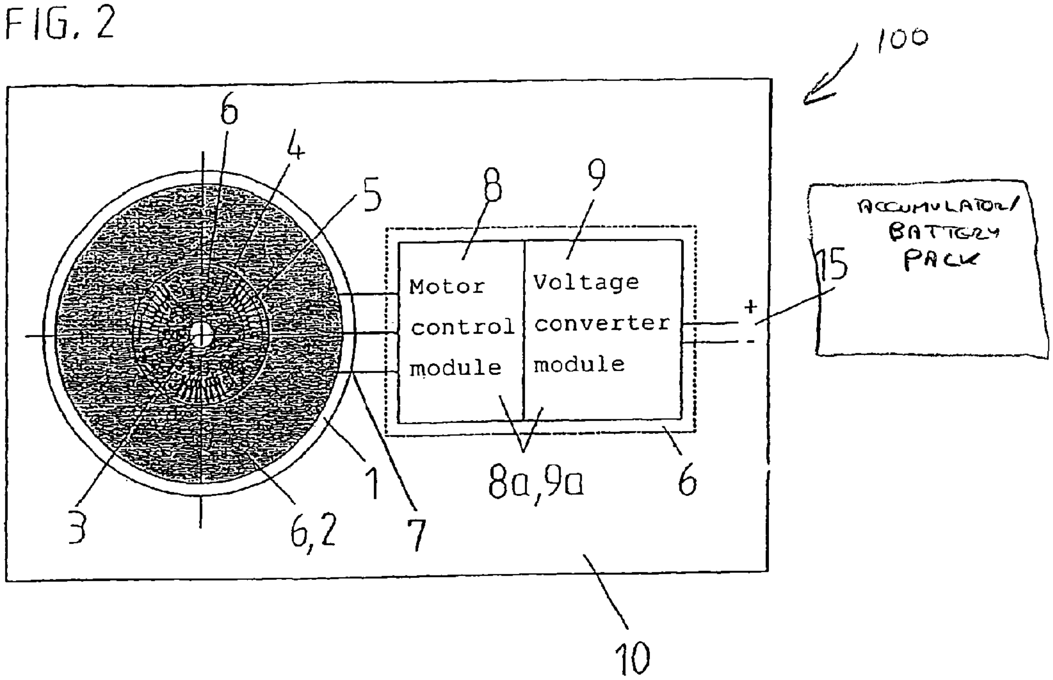
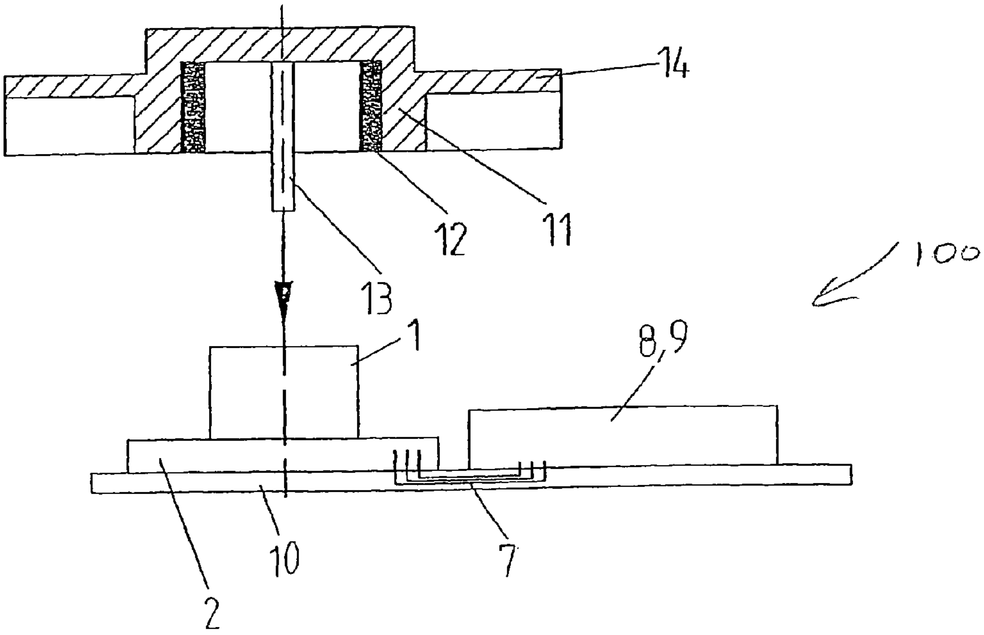
FIG. 1
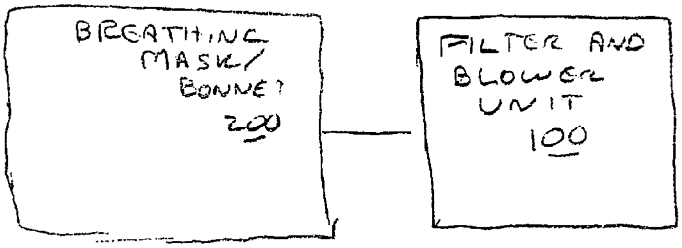
FIG 3

FILTER AND BLOWER UNIT FOR BREATHING MASKS OR BONNETS

BACKGROUND OF THE INVENTION

1. Field of the Invention

This invention relates to a filter and blower unit for breathing masks or bonnets with a breathing air filter that is driven by a direct current motor and designed for use in potentially explosive areas.

2. Background Art

Breathing masks or bonnets supplied with air via a breathing air filter are commonly equipped with a filter and blower unit driven by a direct current motor to increase breathing comfort, that is, to make breathing through the filter material easier and facilitate long-term assignments of the wearer as well as the use of specific filter types.

Filter and blower units are often required to be designed for use in potentially explosive areas. This entails the requirement to design the direct current motor that drives the filter and blower unit in such a way that any sparks that may occur during its operation cannot ignite the potentially explosive atmosphere. Motors of filter and blower units that are no longer considered intrinsically safe due to their high rating and cannot be operated in potentially explosive atmospheres must therefore meet the requirements of the "d" type of protection—i.e. have an explosion-proof enclosure. An explosion-proof enclosure, however, is a disadvantage for filter and blower units as the manufacturing effort for motors of that design is very high due to the required narrow widths of gap and great gap lengths between the motor enclosure opening and the motor shaft, which makes such motors expensive. Blower motors designed according to the "d" type of protection are also quite heavy because of the measures required to neutralize the ignition power that can occur inside the motor enclosure. In addition, they cannot be used in the "O" zone.

Motors not designed according to the "d" type of protection can only be operated in an explosive atmosphere if power input including inductivity are not too high, i.e. still in the intrinsically safe range ("i" type of protection). The high-performance direct current motors used for filter and blower units do not meet this requirement.

SUMMARY OF THE INVENTION

It is an object of the invention to develop a filter and blower for a filter and blower unit to be used in zone "0" potentially explosive atmospheres that is intrinsically safe, can be operated at high performance, and manufactured at comparatively low cost.

The inventive idea starts from an external rotor motor with an internal stator and fixed coils (stator coil module) and fixed electric terminals for the coils as well as a magnetic rotor arranged pivotably on the perimeter of the stator to create a magnetic field, and consists in embedding the electric connecting lines and coil terminals as well as the upstream motor control and voltage converter modules of the motor in a non-conductive casting compound while supplying power at a voltage that is still in the intrinsically safe range and an accordingly higher current for the required motor rating.

A filter and blower unit designed in this way is intrinsically safe as regards power supply, power input, and motor operation despite the fact that its high output is above the criteria of intrinsic safety; it is potentially of simple design to be manufactured easily and at low cost, it is potentially more light weight than filter and blower units designed according to the "d" type of protection and can be used in a zone "0" potentially explosive atmosphere that has the highest safety requirements.

BRIEF DESCRIPTION OF THE DRAWINGS

An embodiment of the invention is explained in greater detail below with reference to the figures. Wherein:

FIG. 1 shows a lateral view of a filter and blower unit with power supply, a partially sectional view and exploded diagrammatic view, FIG. 2 shows a top view of the stator and the power supply of the direct current motor for the filter and blower; and FIG. 3 schematically shows a breathing mask/bonnet with the filter and blower unit in FIGS. 1 and 2 operatively associated therewith.

DETAILED DESCRIPTION OF THE DRAWINGS

The filter and blower unit 100 is designed with an external rotor motor in which the armature is a fixed stator coil module 1 that is fixedly mounted on a stator circuit board 2. The stator coil module 1 includes coil cores 4 with a coil 5 would onto each of them that are arranged concentrically around a bearing shell 3. The components, electric leads and terminals of the stator coil module 1 and the stator circuit board 2 are embedded in a non-conductive casting compound 6. Via electric connecting lines 7, the stator circuit board 2 is connected to a motor control module 8 and a voltage converter module 9 whose circuit bards 8_a_, 9_a_ are also embedded in a casting compound. The stator coil module 1 and the motor control and voltage converter modules 8, 9 are mounted on a base circuit board 10 on which the connecting lines 7 are also embedded in a non-conductive casting compound the stator coil module 1 is encompassed on its periphery by a magnetic rotor 12 in a pot-type case 11 to generate a magnetic field, said rotor being rotatably mounted around the stator coil module 1 using a shaft 13 centered in the pot-type case 11 and supported by the bearing shell 3. Blades 14 are attached to the outer perimeter of the pot-type case 11 that can be rotated around the stator coil module 1.

As the blower motor (direct current motor) used is an external rotor motor in which both the coils 5 and their connections to the voltage source 15 are fixed and embedded in a casting compound 6, electric output emerging during operation cannot get outside, which means that the direct current motor is intrinsically safe even without the otherwise required explosion-proof enclosure according to the "d" type of protection. A voltage converter module 9 that provides a high motor output in excess of the limits of intrinsic safety is located upstream of the motor control module 8 for power supply and direction of rotation identification and is also shielded by a casting compound, making this portion of power supply intrinsically safe as well. Power is supplied to the voltage converter module 9 at a still intrinsically safe current to voltage ratio, i.e. at a voltage of, for example, 6 to 8 V that still meets the requirements of intrinsic safety, running openly from an intrinsically safe accumulator or battery pack 15, and a higher current that corresponds to the required motor output.

In the embodiment described above, the motor of the filter and blower unit is considered intrinsically safe in all its parts—from power input to operation—and can be used in potentially explosive areas such as zone "0" potentially explosive atmospheres where there is a lasting or frequent explosion hazard. In addition, the blower unit lends itself to a simple and lightweight design.

As shown in FIG. 3, the filter and blower unit 100 is operatively associated with a breathing mask/bonnet 200. The precise construction of the breathing mask/bonnet 200 is not critical to the present invention. Those skilled in this art are familiar with numerous constructions currently available as well as structure through which the filter and blower unit 100 can be operatively associated therewith to assist the breathing of a user.

The invention claimed is:

1. A filter and blower unit for breathing masks or bonnets with a breathing air filter that is driven by a direct current motor and designed for use in potentially explosive areas, characterized in that the direct current motor comprises a fixed stator coil module and a magnetic rotor rotating around the peripheral surface of said stator coil module, in that the coils located at the stator coil module and their electric terminals are embedded in a non-conductive casting compound, in that a motor control module and a voltage converter module are located upstream of the stator coil module for power input via shielded electric lines that are also embedded in a non-conductive casting compound, and in that the required power is supplied at a current to voltage ratio at which the voltage does not exceed the value required for intrinsic safety.

2. The filter and blower unit according to claim 1, characterized in that the magnetic rotor comprises a shaft centered in a pot-type case that is pivoted in a bearing shell formed in the center of the stator coil module as well as magnets attached peripherally to its inner surface, and blades attached peripherally to its outer surface.

3. The filter and blower unit according to claim 1, characterized in that the stator coil module, the motor control module and the voltage converter module are located on a base circuit board on which the electric connecting lines run internally or are embedded in a casting compound.

4. The filter and blower unit according to claim 1, characterized in that power is supplied from an intrinsically safe accumulator or battery pack.

5. The filter and blower unit according to any of claims 1-4, in combination with a breathing mask or bonnet with which the filter and blower unit is operatively associated to assist breathing of a user.

* * * * *